(12) United States Patent
Glover et al.

(10) Patent No.: US 7,959,441 B2
(45) Date of Patent: Jun. 14, 2011

(54) LASER BASED ENHANCED GENERATION OF PHOTOACOUSTIC PRESSURE WAVES IN DENTAL AND MEDICAL TREATMENTS AND PROCEDURES

(75) Inventors: Douglas L. Glover, Phoenix, AZ (US);
Enrico E. DiVito, Scottsdale, AZ (US);
Kemmons A. Tubbs, Mesa, AZ (US);
Mark P. Colonna, Whitefish, MT (US)

(73) Assignee: Medical Dental Advanced Technologies Group, L.L.C., Scottsdale, AZ (US)

( * ) Notice: Subject to any disclaimer, the term of this patent is extended or adjusted under 35 U.S.C. 154(b) by 102 days.

(21) Appl. No.: 11/704,655

(22) Filed: Feb. 9, 2007

(65) Prior Publication Data

US 2008/0050702 A1      Feb. 28, 2008

Related U.S. Application Data

(60) Provisional application No. 60/840,282, filed on Aug. 24, 2006.

(51) Int. Cl.
*A61C 5/02* (2006.01)

(52) U.S. Cl. .......................................... 433/224; 433/29

(58) Field of Classification Search ................ 433/29, 433/224
See application file for complete search history.

(56) References Cited

U.S. PATENT DOCUMENTS

| | | | |
|---|---|---|---|
| 4,676,586 A * | 6/1987 | Jones et al. | 385/33 |
| 4,985,027 A * | 1/1991 | Dressel | 606/15 |
| 5,116,227 A | 5/1992 | Levy | |
| 5,173,049 A * | 12/1992 | Levy | 433/215 |
| 5,188,532 A * | 2/1993 | Levy | 433/216 |
| 5,267,995 A * | 12/1993 | Doiron et al. | 606/15 |
| 5,324,200 A | 6/1994 | Vassiliadis et al. | |
| 5,639,239 A | 6/1997 | Earle | |
| 5,968,039 A * | 10/1999 | Deutsch et al. | 606/17 |
| 6,162,052 A | 12/2000 | Kokobu | |
| 7,261,561 B2 * | 8/2007 | Ruddle et al. | 433/122 |
| 2001/0041324 A1 * | 11/2001 | Riitano | 433/102 |
| 2002/0090594 A1 * | 7/2002 | Riitano et al. | 433/224 |
| 2002/0183728 A1 | 12/2002 | Rosenberg et al. | |
| 2003/0013064 A1 | 1/2003 | Zirkel | |
| 2003/0236517 A1 * | 12/2003 | Appling | 606/7 |
| 2004/0038170 A1 | 2/2004 | Hiszowicz et al. | |
| 2004/0193236 A1 | 9/2004 | Altshuler | |
| 2004/0224288 A1 * | 11/2004 | Bornstein | 433/224 |

\* cited by examiner

*Primary Examiner* — Cris L Rodriguez
*Assistant Examiner* — Eric Rosen
(74) *Attorney, Agent, or Firm* — Luedeka, Neely & Graham, P.C.

(57) ABSTRACT

A laser tip, and method for the use thereof, is described for utilization in medical and dental applications. Specifically, a tip with an increased photoacoustic wave emission capability is formed by beveling the tip and further enhanced by stripping the adjacent sheath. Preferably, this conic and/or stripped tip section is surface modified, for example, by texturing, derivatization or metalization. In the field of endodontics the tip is inserted into a solution that has been introduced into a root canal and the pulsed laser is fired. The resulting generation of an enhanced photoacoustic wave propagates through the solution. These photoacoustic waves turbulently clean the interior of the root and lateral canal systems and/or causes cell lysis and dissolution of inorganics in biotic systems.

8 Claims, 4 Drawing Sheets

LASER BASED ENHANCED GENERATION OF PHOTOACOUSTIC PRESSURE WAVES IN DENTAL AND MEDICAL TREATMENTS AND PROCEDURES

This application is a provisional application Ser. No. 60/840,282 filed on Aug. 24, 2006.

FIELD OF THE INVENTION

The present invention is related to the field of dentistry, medicine and veterinary medicine. More specifically, the present invention is a method and device for rapid molecular modification of biological structures for dental, medical and veterinary procedures and/or treatments. Additionally, the present invention is an integration of lasers, photoacoustics, photoacoustic (PA) waves, and other sciences with treatments and procedures in dentistry, medicine and veterinary medicine.

BACKGROUND OF THE INVENTION

Recent advances in the fields of dentistry, medicine, and veterinary medicine necessitate functional and efficient implementation of therapies during exploratory and restructuring procedures. Approaches of interest combine efficiency and esthetics with the inherent utility of the investigative area. Of specific interest is the arena the dental root canals that while rapidly increasing in volume throughout the world have lagged in gaining concerted integration of recent scientific advancements.

When performing root canals it is desirable to efficiently debride or render harmless all tissue, bacteria, and/or viruses within the root canal system. As shown in FIG. 1A and FIG. 1B (FIG. 1B is a simplified representation of FIG. 1A), a tooth root 5 of the root canal system includes the main root canal 1 and all of the accessory or lateral canals 3 that branch off of the main canal 1 generally towards the jaw bone 7. Some of these accessory canals are very small and extremely difficult to reach in order to eliminate any bacteria and/or viruses. Such accessory canals 3 may bend, twist, change cross-section and/or become long and small as they branch off from the main canal 1, making them very difficult to access or target therapeutically.

The accepted dental procedure is to mechanically pull out the main canal nerve 1 thereby separating it from the accessory canal nerves 3 (which stay in place) then filing out the main canal 1 with a tapered file. This action leaves an undesirable smear layer along the main canal 1 and actually plugs some of the accessory canal 3 openings, which potentially trap harmful bacteria or other harmful maladies. This is very undesirable. The dentist must chemo-mechanically debride both main 1 and accessory canals 3, including the smear layer produced by the filing. Often this is done with a sodium hyperchlorite solution and various other medicaments that are left in the root canal system for 30 to 45 minutes. This current methodology does not necessarily debride or render harmless all of the accessory root canals 3 because of the difficulty in first cleaning off the smear layer then negotiating some of the smaller twisted lateral canals. As a result many treatments using this method fail over time due to reoccurring pathology. This often requires retreatment and/or sometimes loss of the tooth.

Therefore, there is a present and continuing need for new and improved dental, medical, and veterinary procedures that address the above problems.

SUMMARY OF INVENTION

It is an object of the present invention to provide new medical, dental and veterinary devices, treatments and procedures.

It is another object of the present invention to provide a device for producing a photoacoustic wave used in endodontal treatment of tooth interiors comprising a laser system having a wavelength of at least 1500 nm and power of at least 0.5 Watt, a sheath coupled at one end to the laser system said sheath comprising a laser fiber optic and a treatment fluid lumen, both running the length of the sheath and exiting the sheath at a distal end, said laser fiber optic having a flat, blunt or modified tip and whereby inserting the tip into the treatment fluid delivered into root canal produces a photoacoustic wave as the laser is pulsed.

It is yet another object of the present invention to provide a method for endodontal treatment of tooth interiors comprising the steps of: providing a laser having a wavelength of at least 1500 nm and at least 0.5 Watt; providing a laser fiber optic coupled to the laser, said laser fiber optic having a flat, blunt or modified tip; inserting the tip of the laser fiber optic into a root canal in a tooth; treating the interior root canal by creating a photoacoustic wave front in the interior of the root canal using the at least 1500 nm at least 0.5 Watt laser energy; withdrawing the tip of the laser fiber optic from the root canal; and sealing root canal.

The novel features that are considered characteristic of the invention are set forth with particularity in the appended claims. The invention itself, however, both as to its structure and its operation, together with the additional objects and advantages thereof, will best be understood from the following description of the preferred embodiment of the present invention when read in conjunction with the accompanying drawings. Unless specifically noted, it is intended that the words and phrases in the specification and claims be given the ordinary and accustomed meaning to those of ordinary skill in the applicable art or arts. If any other meaning is intended, the specification will specifically state that a special meaning is being applied to a word or phrase. Likewise, the use of the words "function" or "means" in the Description of Preferred Embodiments is not intended to indicate a desire to invoke the special provision of 35 U.S.C. §112, paragraph 6 to define the invention. To the contrary, if the provisions of 35 U.S.C. §112, paragraph 6, are sought to be invoked to define the invention (s), the claims will specifically state the phrases "means for" or "step for" and a function, without also reciting in such phrases any structure, material, or act in support of the function. Even when the claims recite a "means for" or "step for" performing a function, if they also recite any structure, material or acts in support of that means of step, then the intention is not to invoke the provisions of 35 U.S.C. §112, paragraph 6. Moreover, even if the provisions of 35 U.S.C. §112, paragraph 6, are invoked to define the inventions, it is intended that the inventions not be limited only to the specific structure, material or acts that are described in the preferred embodiments, but in addition, include any and all structures, materials or acts that perform the claimed function, along with any and all known or later-developed equivalent structures, materials or acts for performing the claimed function.

DETAILED DESCRIPTION OF THE DRAWINGS

FIG. 1a and 1b illustrates a root canal system including the main root canal and all of the accessory or lateral canals that branch off of the main canal (1a). Some of these accessory canals are very small and extremely difficult to reach in order to eliminate any bacteria and/or viruses. Such accessory canals may bend, twist, change cross-section and/or become long and small as they branch off from the main canal, making them very difficult to access or target therapeutically. 1b is a simplified graphical representation of the same.

DESCRIPTION OF THE PREFERRED EMBODIMENTS

The present invention is useful for treating dental, medical, and veterinary problems; primarily dental surface preparations. The present invention uses enhanced photoacoustic wave generation in dental, medical, and veterinary application during procedures that otherwise face reoccurring infection, inefficient performance and at an increase in expenses. The result of this invention has the potential to increase the effective cleaning of the root canal and accessory canals and the potential to reduce future failures over time.

Figure 1A:
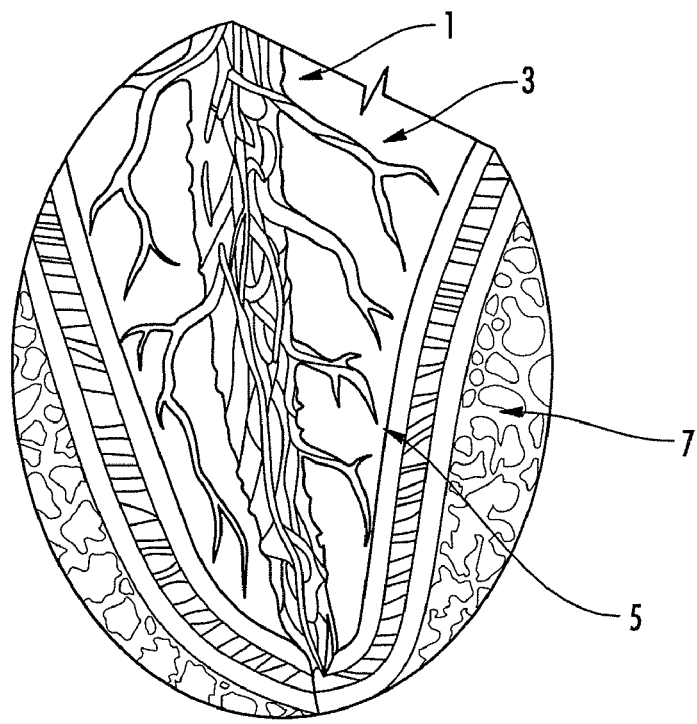
Figure 1B:
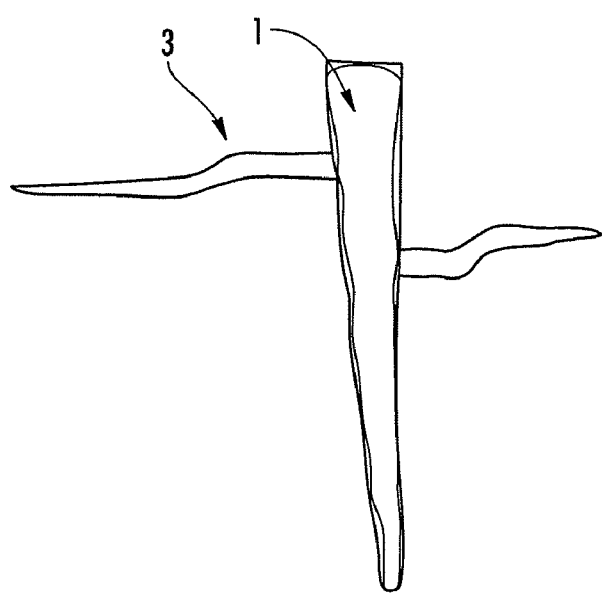
Figure 2:
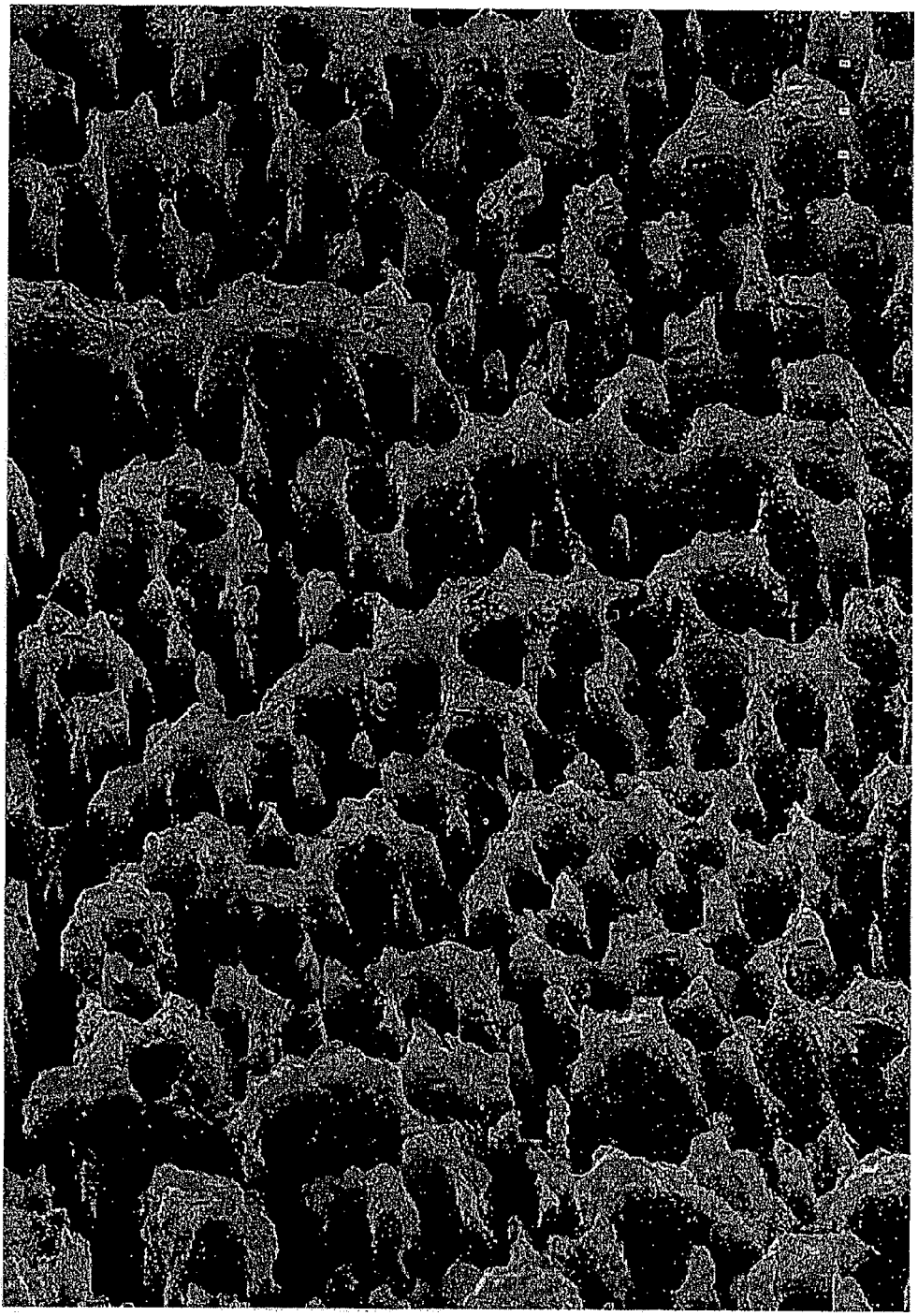
FIG. 2 is a Scanning Electron Micrograph (SEM) clearly illustrating internal reticular surfaces created by the present invention, which are preserved and sterilized for subsequent filling and embalming, i.e. using rubber, gutta-percha, latex, etc.
Figure 3:
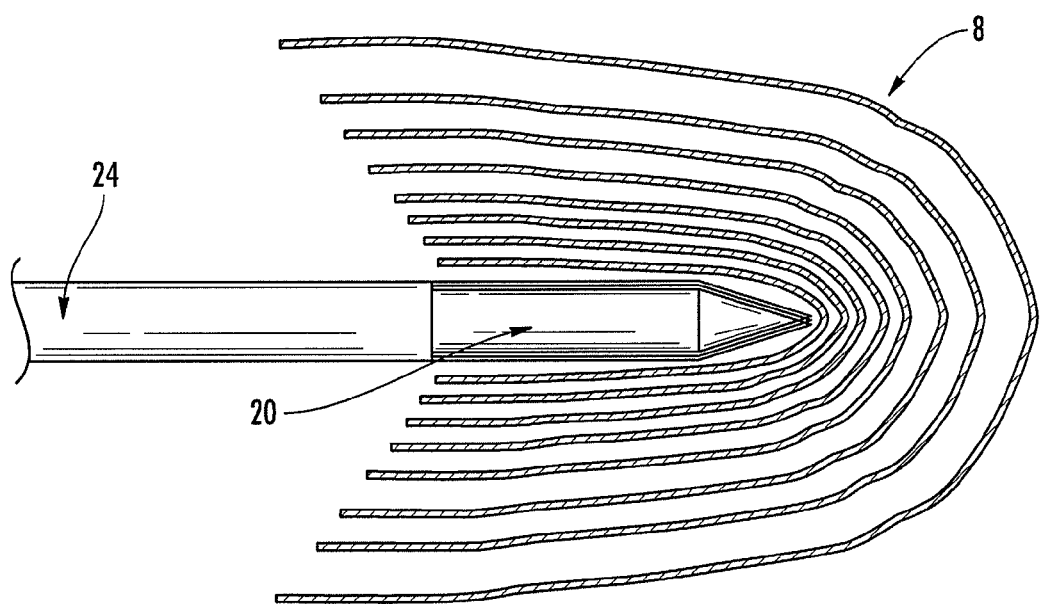
FIG. 3 is an illustration of a laser fiber tip preferably used according to the present invention.
Figure 4:
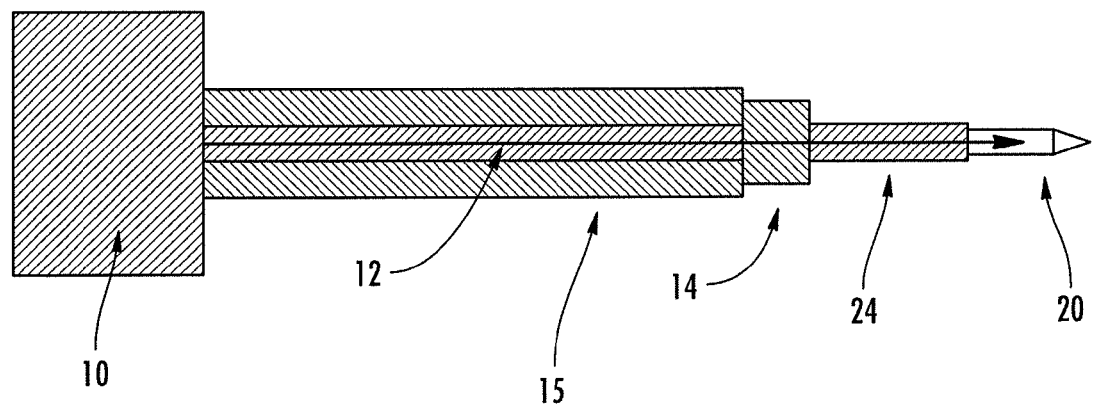
FIG. 4 is an illustration of the system according to the present invention.

As shown in FIG. 3 and FIG. 4, the most preferred embodiment of the present invention utilizes an energy source which is preferably a pulsed laser energy that is coupled to a solution in such a fashion that it produces an enhanced photoacoustic pressure wave 8. The laser light is delivered using a commercially available laser source 10 and an optical light fiber 15 attached at a proximate end to the laser source 10 and has an application tip 20 at the distal end. The application tip 20 may be flat or blunt, but is preferably a beveled or tapered tip having a taper angle between 10 and 90 degrees. Preferably any cladding 24 on the optic fiber is stripped from approximately 2-12 mm of the distal end. The taper angle of the fiber tip 20 and removal of the cladding 24 provide wider dispersion of the laser energy 12 over a larger tip area and consequently produces a larger photoacoustic wave. The most preferred embodiment of the application tip 20 includes a texturing or deriviatization of the beveled tip 20, thereby increasing the efficacy of the conversion of the laser energy 12 into photoacoustic wave energy within the solution. A coupling ferrule 14 may be used to interchange different applicator tips. It should be noted that in the present invention this tapered tip 20, the surface treatment, and the sheath or cladding 24 stripping is not for the purpose of diffusing or refracting the laser light 12 so that it laterally transmits radiant optical light energy to the root surface. In the current invention these features are for the sole purpose of increasing the photoacoustic wave.

Herein derivatization means a technique used in chemistry that bonds, either covalently or non-covalently, inorganic or organic chemical functional group to a substrate surface.

It was found that the photoacoustic coupling of the laser energy to the solution provides enhanced penetration of the solution into the root canal and accessory canals, thereby allowing the solution to reach areas of the canal system that are not typically accessible.

The photoacoustic (PA) wave is generated when the laser energy transitions from the tip (usually quartz or similar material) of the laser device into the fluid (such as water, EDTA, or the like. The transmission from one medium to another is not 100% efficient and some of the light energy is turned into heat near the transition that the light makes from one media to the other. This heating is very rapid, locally heating some of the molecules of the fluid very rapidly, resulting in molecule expansion and generating the photoacoustic wave. In a pulsed laser, a wave is generated each time the laser is turned on, which is once per cycle. A 10 HZ pulsed laser then generates 10 waves per second. If the power level remains constant, the lower the pulse rate, the greater the laser energy per pulse and consequently the greater the photoacoustic wave per pulse.

The photoacoustic effect creates sound (pressure) waves that can potentially propagate throughout both the media and localized structure, e.g., the main root canal and the lateral or accessory canals. These sound waves provide vibrational energy, which expedites the breaking loose of and/or causing cell lysis of the biotics and inorganics in the root canal and lateral canal systems. In addition these vibrational waves help the propagation of the fluids into and throughout the main and lateral canal systems.

In general, light travels in a straight line, however, in a fluid light can be bent and transmitted around corners, but this transmission is minimal compared to the straight-line transmissibility of light. A sonic or shock wave on the other hand is easily transmitted around corners and through passages in a fluid. For example, air is a fluid. If you stood in one room and shined a bright light from that room into a hallway that was at right angles to that room, the intensity of the light would decrease the farther you go down the hallway. If you then went into a room at the end of the hallway and went to a back corner of the room, the light might be very dim. However, if while standing at the same location as the light source, you yelled vocally at the hallway, you could most likely hear the sound in the back corner of the back room. This is because sound is propagated spherically by the vibration of molecules instead of primarily in a straight line like light.

Although the laser light cannot turn corners easily and cannot propagate easily into the lateral canals, the sonic wave produced by the photoacoustic effect is easily transmitted through the lateral canals. Also, since the canals are tapered in a concave fashion, the photoacoustic wave will be amplified as it transverses toward the end of the lateral canals. Since the cross-sectional area of the lateral canals decreases as the wave traverses toward the canal end, the amplitude of the wave increases much as a Tsunami wave increases as it approaches a beach where the cross sectional area of the water channel constantly decreases.

The tip design can affect the magnitude and direction of the produced photoacoustic wave. A tapered tip has the effect of diverting the laser energy over the larger cone area (compared to the circular area of the standard tip) and thereby creating a larger photoacoustic wave. The same applies to any stripped sheath section of the tip.

Testing using a MEMS Pressure sensor:

A small plastic vial was fitted with a fluid connection (bottom of vial at right angles to axis of vial) that was close coupled hydraulically to a miniature MEMS piezo-resistive pressure sensor (Honeywell Model 24PCCFA6D). The sensor output was run through a differential amplifier and coupled to a digital Oscilloscope (Tektronics Model TDS 220). This model oscilloscope will hold a trace on the screen and allow a digital image to be taken of the trace. The vial and sensor were filled with water. The laser tip was submerged below the fluid level in the vial and fired (laser frequency was 10 HZ) at various power setting. A trace was recorded of the resulting photoacoustic pressure waves.

A 170% increase in the photoacoustic wave was observed for the tapered and stripped tip versus the blunt-ended tip. A 580% increase in the photoacoustic wave was observed for textured (frosted) tapered/stripped tip versus the standard blunt-ended tip. The tapered tip has a greater exposed area than the blunt straight tip. The fiber optic is coated with a polyamide sheath, which reflects the laser beam internally, not allowing it to escape and propagating the laser energy down the fiber to the tip. On the straight or blunt-ended tip, the exposed area is the circular cross-sectional area of the end of the tip. On the tapered tip and textured tip the exposed area is the area of the tapered cone, which is greater than the exposed area of the blunt straight tip. This invention is on the ability of these features to increase the photoacoustic wave not to refract or redirect the radiant optical properties of the laser energy. In fact such radiant light energy can fuse the root canal wall surface making it impossible to clean and debride the small passages behind the fused areas.

During a previous experiment, fluid was placed into a Dampen dish located on a Formica surface. The laser tip was placed into the fluid and fired repetitively. The photoacoustic wave vibrated the Dampen dish on the Formica surface making an audible sound. For a specific tip this audible sound increased with an increasing power level of the laser. This implies that the audible sound is somewhat proportional to the amplitude of the photoacoustic wave. This was verified by placing a sound level meter one inch away from the Dampen dish and recording the dB level. Next, the laser power level was held constant and the tip was changed. The tapered and stripped sheath tip produced a greater photoacoustic wave than the standard straight or blunt-end tip. A tapered and stripped tip was then frosted or etched. This tip was tested and showed a greater photoacoustic wave generated than the non-frosted version. This was verified to be true at three different power levels. It would appear that since the power level was held constant, the photoacoustic wave amplitude would also be proportional to the exposed area and the surface treatment.

An increase in photoacoustic wave generation was seen by stripping the polyamide sheath away for 2-12 mm from the tapered end. Although laser light is coherent and travels in a straight line, some light bounces off of the polyamide sheath at an angle. As this light travels down the light path it continues bouncing off of the inside of the polyamide sheath and will eventually exit at an angle to the sheath once the sheath stops and exposes a non sheathed section. Therefore, some of the laser energy would also exit where the polyamide sheath has been removed, just upstream of the tapered tip. A tip with the sheath removed for 2 to 12 mm directly upstream of the tapered section was placed in the above-mentioned test set up.

The photoacoustic wave will propagate primarily perpendicular to the exposed surface and secondarily spherically with respect to the exposed surface. The standard straight end tip would have the PA wave propagating primarily in line with the tip. The tapered tip produced PA wave would be primarily propagated in a more lateral pattern. The tapered tip with the shinned sheath would propagate the PA wave in a more spherical pattern than the other two.

The standard straight blunt end tip would be less desirable because it directs the photoacoustic wave toward the apical end of the tooth and would have more propensities to drive the fluid from the nerve hole in the apical end and outward into the gum which could create medical complications. Since there may be lateral or accessory canals anywhere along the main root canal, it is more desirable to have a spherical wave distribution to direct waves to as many lateral canals as possible. Therefore the tapered tip with the skinned sheath produces a more desirable effect within the tooth.

Resultant Scanning Electron Micrographs (SEM's) show the reticular surface of the dentin to be devoid of infection and malady and allowing for rinsed removal of the debris elements.

The present invention also includes embodiments of the individual components, kits, methods, their manufacture, and their assembly into one singular procedure. Still further herein included are methods and processes for use of the individual components and the integration in biological applications.

All publications and patent applications are herein incorporated by reference to the same extent as if each individual publication or patent application was specifically and individually indicated to be incorporated by reference. Although the present invention has been described in some detail by way of illustration and example for purposes of clarity and understanding, it will be apparent that certain changes and modifications may be practiced within the scope of the appended claims.

The preferred embodiment of the invention is described above in the Drawings and Description of Preferred Embodiments. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventor that the words and phrases in the specification and claims be given the ordinary and accustomed meanings to those of ordinary skill in the applicable art(s). The foregoing description of a preferred embodiment and best mode of the invention known to the applicant at the time of filing the application has been presented and is intended for the purposes of illustration and description. It is not intended to be exhaustive or to limit the invention to the precise form disclosed, and many modifications and variations are possible in the light of the above teachings. The embodiment was chosen and described in order to best explain the principles of the invention and its practical application and to enable others skilled in the art to best utilize the invention in various embodiments and with various modifications as are suited to the particular use contemplated.

What is claimed is:

1. A method for providing a photoacoustic wave therapy for use in endodontic treatments of tooth interiors comprising:
   (a) providing a laser system;
   (b) providing a laser fiber optic operatively coupled to the laser system, said laser fiber optic being substantially cylindrical and untapered from adjacent a proximal end to adjacent a tip which tapers from a circumference of the laser fiber optic to an apex with a surrounding generally conical wall, defining a surrounding generally conical outer surface of said tip and further where the laser fiber optic contains a sheath extending from adjacent the proximal end of the laser fiber optic to a terminus edge thereof spaced proximally from the beginning of said tapered tip and spaced proximally from said apex of said tapered tip toward said proximal end by a distance of from about 2 mm to about 12 mm so that at least the surface of said fiber optic is uncovered over substantially the entirety of said tapered tip and over at least the portion of an outer surface of the substantially cylindrical and untapered part of said fiber optic extending from adjacent said terminus edge to the beginning of the tapered tip;

(c) delivering a treatment liquid into a root canal in a tooth;

(d) submerging at least the tip and the uncovered portion of the outer surface of the substantially cylindrical and untapered part of said laser fiber optic into the treatment liquid so that substantially no laser light may be emitted from the outer surface of said fiber optic into any open space above an upper surface of the liquid in the canal;

(e) treating the interior of the root canal by pulsing a laser through the fiber optic so that laser light is emitted from surfaces thereof uncovered by said sheath generally omnidirectionally to create a series of photoacoustic waves which propagate from said surfaces generally omnidirectionally through the treatment liquid in the interior of the root canal and into contact with adjacent root canal wall surfaces in order to disintegrate material in the root canal, while preserving, cleaning and disinfecting reticular surfaces of the aforesaid adjacent root canal wall surfaces relative to their condition prior to treatment as aforesaid;

(f) withdrawing the tip of the laser fiber optic from the treatment liquid; and (g) sealing the root canal.

2. The method according to claim 1 where substantially the entire surface of the tapered tip is uncovered.

3. The method according to claim 1 where the tapered tip is a surface modified tip comprising a textured surface, a frosted surface, or a derivatized surface.

4. The method according to claim 1 where the laser fiber optic has no cladding or sheath adjacent to the tip.

5. The method of claim 1, wherein the treatment liquid comprises an EDTA solution.

6. The method of claim 1, wherein the treatment liquid comprises water.

7. A method for providing a photoacoustic wave therapy for use in dental or periodontal treatments comprising:

(a) providing a laser system;

(b) providing a laser fiber optic operatively coupled to the laser system, said laser fiber optic being substantially cylindrical and untapered from adjacent a proximal end to adjacent a tip-which tapers from a circumference of the laser fiber optic to an apex with a surrounding generally conical wall, defining a surrounding generally conical outer surface of said tip and further where the laser fiber optic contains a sheath extending from adjacent the laser system to a terminus edge thereof spaced proximally from the proximal end of said tip and spaced proximally from said apex of said tapered tip toward said laser system by a distance of from about 2 mm to about 12 mm so that at least the surface of said fiber optic is uncovered over substantially the entirety of said tapered tip and over at least a portion of an outer surface of the substantially cylindrical and untapered part of said fiber optic extending from adjacent said terminus edge to the beginning of the tapered tip;

(c) delivering a treatment liquid into a root canal, sulcus or tissue space in a mouth;

(d) submerging the tip and the uncovered portion of the laser fiber optic into the treatment liquid;

(e) treating the interior of the root canal, sulcus or tissue space by pulsing a laser through the fiber optic so that laser light is emitted therefrom generally omnidirectionally to create a series of photoacoustic waves which propagate from the outer surface of the fiber optic from at least the portion of the surface extending from the terminus edge to the apex, said waves propagating generally omnidirectionally through the treatment liquid in the interior of the root canal, sulcus or tissue space and into contact with root canal wall surfaces or other adjacent surfaces, tissues, or structures so as to cause disintegration of material in the treatment liquid in the canal, sulcus, or tissue space while preserving, cleaning, and disinfecting internal surfaces of the aforesaid adjacent root canal wall and other adjacent surfaces, tissues, or structures relative to their condition prior to treatment as aforesaid;

(f) withdrawing the tip of the laser fiber optic from the treatment liquid.

8. The method according to claim 7 where substantially the entire surface of the tapered tip is uncovered.

* * * * *